(12) United States Patent  (10) Patent No.: US 7,884,936 B2
Manassen  (45) Date of Patent: Feb. 8, 2011

(54) APPARATUS AND METHODS FOR SCATTERING-BASED SEMICONDUCTOR INSPECTION AND METROLOGY

(75) Inventor: Amnon Manassen, Haifa (IL)

(73) Assignee: KLA-Tencor Corporation, Milpitas, CA (US)

( * ) Notice: Subject to any disclaimer, the term of this patent is extended or adjusted under 35 U.S.C. 154(b) by 271 days.

(21) Appl. No.: 12/182,788

(22) Filed: Jul. 30, 2008

(65) Prior Publication Data

US 2009/0050823 A1    Feb. 26, 2009

Related U.S. Application Data

(60) Provisional application No. 60/957,378, filed on Aug. 22, 2007.

(51) Int. Cl.
*G01B 11/00* (2006.01)
(52) U.S. Cl. .................... 356/401; 356/237.4
(58) Field of Classification Search ................ 356/401, 356/400, 237.4, 239; 250/492.2
See application file for complete search history.

(56) References Cited

U.S. PATENT DOCUMENTS 5,410,400 A * 4/1995 Shishido et al. .......... 356/237.4
7,385,699 B2   6/2008 Mieher et al.

* cited by examiner

*Primary Examiner*—Kiet T Nguyen
(74) *Attorney, Agent, or Firm*—Weaver Austin Villeneuve & Sampson LLP

(57) ABSTRACT

Disclosed are apparatus and methods for inspecting or measuring one or more semiconductor targets. An incident beam is directed towards a first target as the first target substantially, continuously moves such that the incident beam remains directed at such first target during a first time period in which the first target substantially, continuously moves between a first position and a second position. An output beam scattered from the first target, in response to the incident beam being directed towards the first target during the first time period in which the first target substantially, continuously moves between the first and second positions, is detected such that information is obtained from the detected output beam during the first time period. The first time period is selected so that the information that is collected from the detected output beam during such first time period can be used to determine a characteristic of the first target.

22 Claims, 4 Drawing Sheets

APPARATUS AND METHODS FOR SCATTERING-BASED SEMICONDUCTOR INSPECTION AND METROLOGY

CROSS REFERENCE TO RELATED APPLICATIONS

The present application claims priority under 35 U.S.C. §119(e) from U.S. Provisional Patent Application No. 60/957,378 entitled "APPARATUS AND METHODS FOR SCATTERING-BASED SEMICONDUCTOR INSPECTION AND METROLOGY" filed Aug. 22, 2007, the entire disclosure of which is incorporated herein by reference for all purposes.

BACKGROUND OF THE INVENTION

The invention described herein relates generally to semiconductor metrology and inspection. More specifically, it relates to metrology or inspection that employ scanning of a target with an incident beam.

Generally, the industry of semiconductor manufacturing involves highly complex techniques for fabricating integrated circuits using semiconductor materials which are layered and patterned onto a substrate, such as silicon. Due to the large scale of circuit integration and the decreasing size of semiconductor devices, the device must comply with rigorous specification requirements prior to shipment of the device to the end users or customers.

Typically, particular parameters are measured or characterized within special test structures or targets using a metrology or inspection tool. By way of example, multiple targets are designed to measure misalignment or overlay errors between two adjacent layers. In an inspection or metrology process, an incident beam is usually directed towards a particular spot, which includes a first target. After the incident beam reacts with the first target, the output beam is then collected from the first target. The incident beam is required to remain at the first target until enough information is collected into the output beam scattered from the first target. The collected output beam can then be analyzed to determine various characteristics regarding the first target.

After the first target is characterized, a second target can then be moved under the incident beam so that the second target can then be characterized. Typically, multiple target characterization is realized by applying discrete movement shifts to a wafer-carrying stage so that a first target is moved in a single movement to a position under the incident beam. While the first target is characterized, the first target remains stationary. After characterization of the first target, the wafer stage is then moved again in a discrete amount so that a second target is moved to a position under the beam. While the second target is being characterized, the second target also remains stationary under the incident beam. These discrete movements require complex acceleration and deceleration mechanisms. Additionally, the time for performing these discrete wafer movements and characterization of each target can be significant.

It would be beneficial to provide improved mechanisms for performing metrology or inspection on semiconductor targets or the like.

SUMMARY OF THE INVENTION

In one embodiment, a method of inspecting or measuring one or more semiconductor targets is disclosed. An incident beam is directed towards a first target as the first target substantially, continuously moves such that the incident beam remains directed at such first target during a first time period in which the first target substantially, continuously moves between a first position and a second position. An output beam scattered from the first target, in response to the incident beam being directed towards the first target during the first time period in which the first target substantially, continuously moves between the first and second positions, is detected such that information is obtained from the detected output beam during the first time period. The first time period is selected so that the information that is collected from the detected output beam during such first time period can be used to determine a characteristic of the first target. The characteristic of the first target is determined based on the detected output beam.

In a specific implementation, the incident beam is an optical beam. In a further aspect, directing the incident beam at the first target during the first time period is accomplished by titling one or more illumination mirrors in a path of the incident beam so that the incident beam's movement is synchronized with the first target's continuous movement between the first and second positions so that the information, that can be used to determine a characterization of the first target, is obtained from the detected output beam during the first time period. In yet a further aspect, detecting the output beam from the first target during the first time period is accomplished by titling one or more output mirrors in a path of the output beam so that the output beam is detected by a same area of detector during the first time period.

In another implementation, the incident beam is an electron beam. In a further aspect, directing the incident beam at the first target during the time period is accomplished by configuring an incident scanning system in a path of the incident beam so that the incident beam's movement is synchronized with the first target's substantially, continuous movement between the first and second positions so that the information, that can be used to determine a characterization of the first target, is obtained from the detected output beam during the first time period. In another aspect, detecting the output beam from the first target during the time period is accomplished by configuring an output scanning system in a path of the output beam so that the output beam is detected by a same area of detector during the first time period.

In one embodiment, the characterization includes one or more of the following: an overlay error, a film thickness, or a critical dimension measurement. In a further implementation, after the first time period, the incident beam is directed towards a second target as the second target substantially, continuously moves such that the incident beam remains directed at such second target during a second time period in which the second target moves between the first position and the second position. An output beam scattered from the second target, in response to the incident beam being directed towards the second target during the second time period in which the second target moves between the first and second positions, is detected such that information is obtained from the detected output beam during the second time period. The second time period has a substantially equal duration as the first time period and is selected so that the information that is obtained from the detected output beam during such second time period can be used to determine a characteristic of the second target. The characteristic of the second target is determined based on the detected output beam from the second target. In a further aspect, the incident beam is initially directed at the second target when the second target is at a substantially same position as the first target's position at which the incident beam was initially directed towards the first target.

In an alternative embodiment, the invention pertains to an apparatus for inspecting or measuring one or more semiconductor targets. The apparatus includes one or more processors and one or more memory, wherein at least one of the processors and memory are adapted for performing one or more of the above described techniques.

These and other features and advantages of the present invention will be presented in more detail in the following specification of the invention and the accompanying figures which illustrate by way of example the principles of the invention.

DETAILED DESCRIPTION OF SPECIFIC EMBODIMENTS

Reference will now be made in detail to a specific embodiment of the invention. An example of this embodiment is illustrated in the accompanying drawings. While the invention will be described in conjunction with this specific embodiment, it will be understood that it is not intended to limit the invention to one embodiment. On the contrary, it is intended to cover alternatives, modifications, and equivalents as may be included within the spirit and scope of the invention as defined by the appended claims. In the following description, numerous specific details are set forth in order to provide a thorough understanding of the present invention. The present invention may be practiced without some or all of these specific details. In other instances, well known process operations have not been described in detail in order not to unnecessarily obscure the present invention.

In general, the wafer and its targets that are disposed thereon undergo continuous movement while an incident beam from the measurement system "escorts" each target until enough information is collected in an output beam that is scattered from such target in order to determine a characteristic, such as overlay, of such target. The amount of information that is needed in order to determine a characteristic of a target depends on a number of factors, such as the incident beam intensity or flux, the efficiency of the detector that is used to detect the output beam from each target, system losses, target reflectivity, etc. After enough information is collected, the incident beam then escorts a next continuously moving target as information is collected from such next target.

Figure 1:
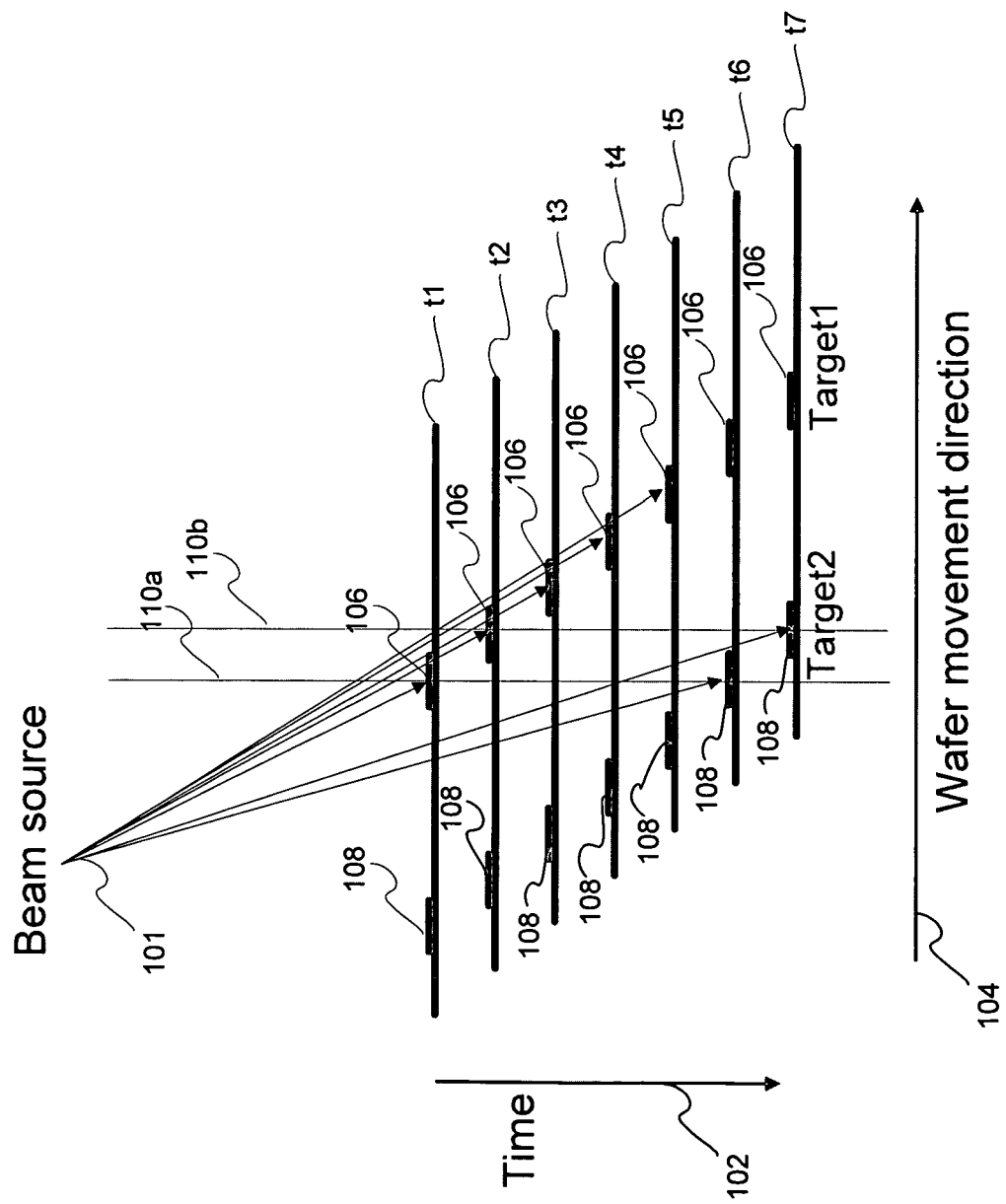
FIG. 1 is a diagrammatic representation of two targets undergoing an escorting procedure in accordance with one embodiment of the present invention.

FIG. 1 is a diagrammatic representation of two targets undergoing an escorting measurement procedure in accordance with one embodiment of the present invention. As shown, a first target 106 and a second target 108 move in direction 104 with the passage of time 102. The wafer and its two targets continuously move in direction 104 for the time period t1 through t7. For the same time frame, the incident beam 101 follows either the first target 106 or the second target 108. At time t1, the incident beam 101 impinges on the first target 106 when the first target is at position 110a. The incident beam 101 continues to impinge on the first target 106 as it moves from position 110a to position 110b at time t2.

The incident beam 101 continues to escort the first target 106 from times t1 through t5. The period of time in which the incident beam escorts a target is generally selected so that enough information is collected from the first target 106 so as to determine a characteristic of the first target. For instance, an output beam that is scattered from the target in response to the incident beam is detected and used to determine an overlay error, a film thickness, or a critical dimension (CD) measurement. In these examples, the incident beam needs to scatter off the target long enough to result in an output beam that can be used to determine overlay, film thickness, or CD. The detector generally has to accumulate a significant signal above its noise level while not going into saturation due to the collection of the output beam scattered off a target with a given reflectivity and passing through a system with a given loss. Accordingly, the time period that is used for the incident beam to escort a particular target can depend on various factors, such as the incident beam's intensity and/or flux and the efficiency of the detector used to detect the output beam.

In certain configurations, it may be desirable to have the incident beam jump to a next target when the next target is at a same initial position as the previous target. In the illustration of FIG. 1, at time t6 the second target 108 is in the same position 110a at which the first target was positioned at time t1. That is, the position of the first target 106 at time t1 is substantially the same as the position of the second target 108 at time t6. As described further below, this arrangement entails that the mechanisms that are used to tilt or deflect the incident beam are configured in a same way during each escort time period for each target. In a preferred embodiment, the arrangement includes mechanisms for maintaining a same incident angle and beam profile for each escorted target. Although this arrangement simplifies the configuration of the tilting or deflecting mechanisms for the incident beam (and corresponding scattered output beam), other configurations may be utilized that do not result in a same configuration sequence during each escort time period for each target.

Any suitable mechanism may be utilized to adjustably tilt or deflect the incident beam and resulting scattered output beam so as to escort each target as information is collected from each target. Examples of optical mechanisms for adjustably tilting or deflecting an optical incident beam or output beam include mirrors or other reflective surfaces which can adjustably tilt an optical beam, or a mechanism for linear translation of the beam over the systems pupil, wherein the pupil is characterized such that there is a transformation between position on the pupil and angle on the target, etc. Examples of suitable optical systems that may employ techniques of the present invention include one or more of the following optical tools: reflectometers, elipsometers, optical systems that provide multiple wavelengths, multiple beams, and/or multiple angles of incidence, etc.

In particular electron microscopy systems, the techniques of the present invention may be implemented by adjustably deflecting the incident electron beam by selectively configuring one or more of the following components: alignment coils, scanning coils, etc. Examples of electron microscopy systems that may employ techniques of the present invention include scanning electron microscopes (SEM's), transmission electron microscopes (TEM's), etc.

Figure 2:
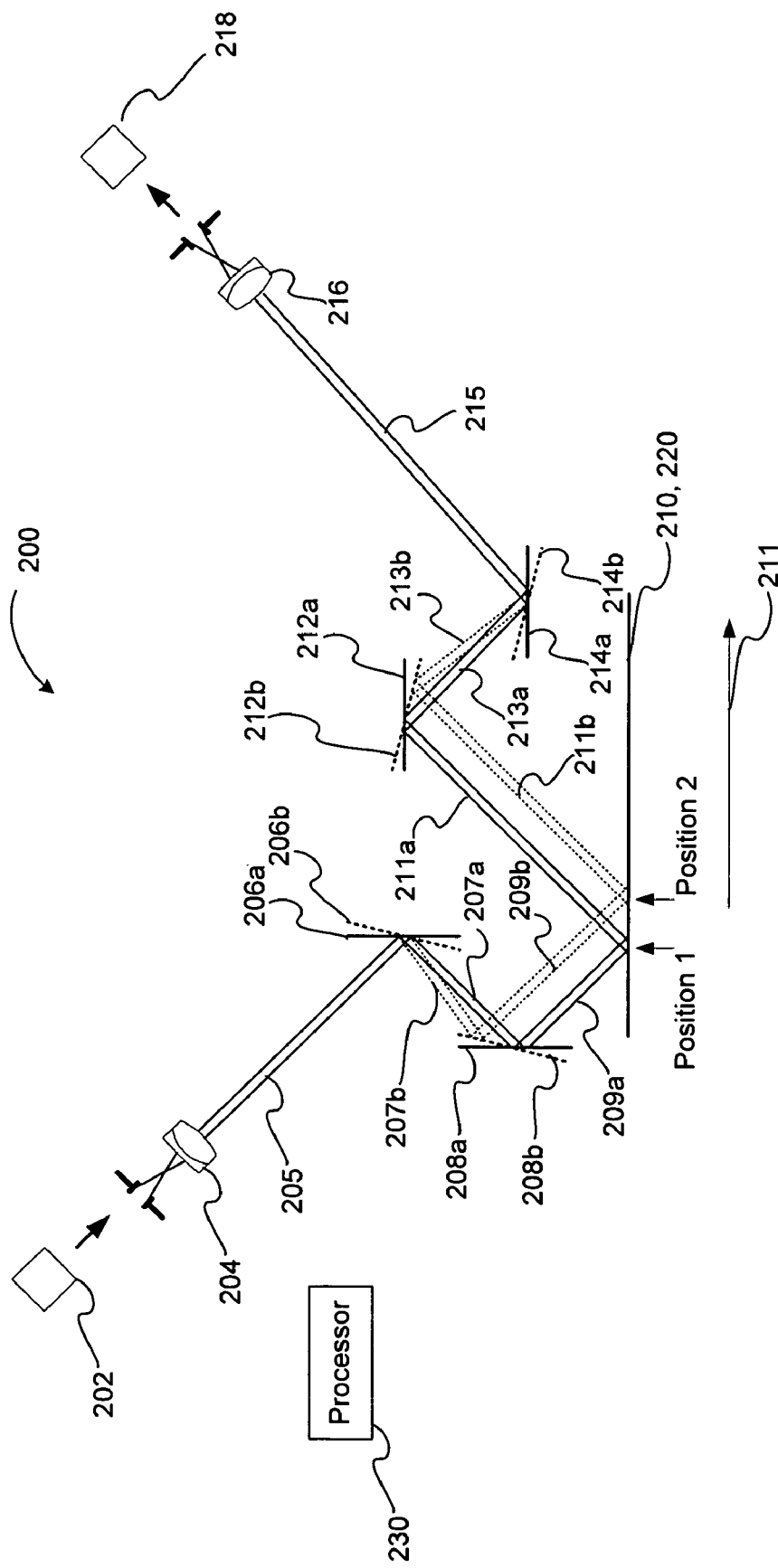
FIG. 2 is a diagrammatic representation of an optical system in accordance with a specific implementation of the present invention.

FIG. 2 is a diagrammatic representation of an optical system 200 in accordance with a specific implementation of the present invention. As shown, the optical system 200 may include a beam generator 202 for generating one or more optical beams 205, which are directed by incident optical elements 204, 206, and 208 towards sample 210. The optical system 200 also may include output optical elements 212, 214, and 216 for directing one or more output beams, which are scattered from the sample 210 in response to the one or more incident beams, towards one or more detectors 218.

In general, the incident optical elements are configured to direct the one or more optical beams to escort or track a specific target on the sample 210 as the target moves, e.g., in direction 211, via movement of stage 220 upon which the sample is positioned. In the illustrated embodiments, the incident optical elements include adjustably incident tilting mirrors 206 and 208 which can be adjustably tilted so as to direct the incident beam to track particular targets of the sample 210. Of course, the incident beam may be reflected by any number of tilting mirrors so as to escort specific targets as such targets continuously move. Different tilt positions of the tilting mirrors 206 and 208 reflect an incident beam towards different positions along a particular axis, such as x axis, while the sample is moving along such axis. The different tilt positions may also preferably result in a same incident angle and beam profile. However, since the sample 210 is moving in synchronicity with respect to the incident beam, the incident beam can be directed to track or follow the same target of the sample.

As shown, mirror 206 is initially positioned at a first tilt position 206a so that incident beam 205 is reflected along path 207a. Mirror 208 is initially positioned at a first tilt position 208a so that incident beam 207a is reflected along path 209a towards Position 1. A first target of sample 210 may also be initially positioned at Position 1. As the sample 210 and the first target moves from Position 1 to Position 2, mirror 206 moves from tilt position 206a to 206b and mirror 208 continuously moves from tilt position 208a to 208b such that the incident beam is continuously moved from path 207b to 209b and, as a result, continuously moves from Position 1 to Position 2. Thus, the first target can move continuously between Positions 1 and 2 synchronously with the incident beam. After the first target reaches Position 2, another second target has preferably moved to Position 1 and the tilting mirrors 206 and 208 can be repositioned to tilt positions 206a and 208a, respectively, to begin tracking of the second target. The tilting mirrors are then tilted continuously from tilt positions 206a and 208a to tilt positions 206b and 208b to thereby track the second target as it moves continuously from Position 1 to Position 2.

In a like manner, the output optical elements may include output tilting mirrors 212 and 214 that are adjusted to continuously move between positions 212a and 212b and between positions 214a and 214b, respectively, as the targets move between Positions 1 and 2. As a target moves from Positions 1 to 2 and is tracked by the incident beam, the resulting output beams can be synchronously directed towards detector 218. For instance, when incident beam 209a impinges on target at Position 1, the scattered output beam 211a reflects from mirror 212 at tilt position 212a along path 213a, onto tilt mirror 214 at tilt position 214a, and is reflected along path 215 towards detector 218. Likewise, when incident beam 209b impinges on target at Position 2, the scattered output beam 211b reflects from mirror 212 at tilt position 212b along path 213b, onto tilt mirror 214 at tilt position 214b, and is reflected along the same path 215 towards detector 218. Accordingly, the output tilting mirrors may be adjustably tilted so that the output beam reflected from a continuously moving target reaches a substantially same area of the detector while such target is being tracked by the incident beam.

The system 200 may also include one or more processors 230, which may include any suitable hardware, such as one or more computer processing units and/or memory devices, and/or software for controlling various components of the system 200. By way of examples, processor 230 can be configured to control various control or analysis operations such as beam generation, stage movement, incident and output beam movement (e.g., escorting), detector settings, signal processing and analysis, etc.

Figure 3:
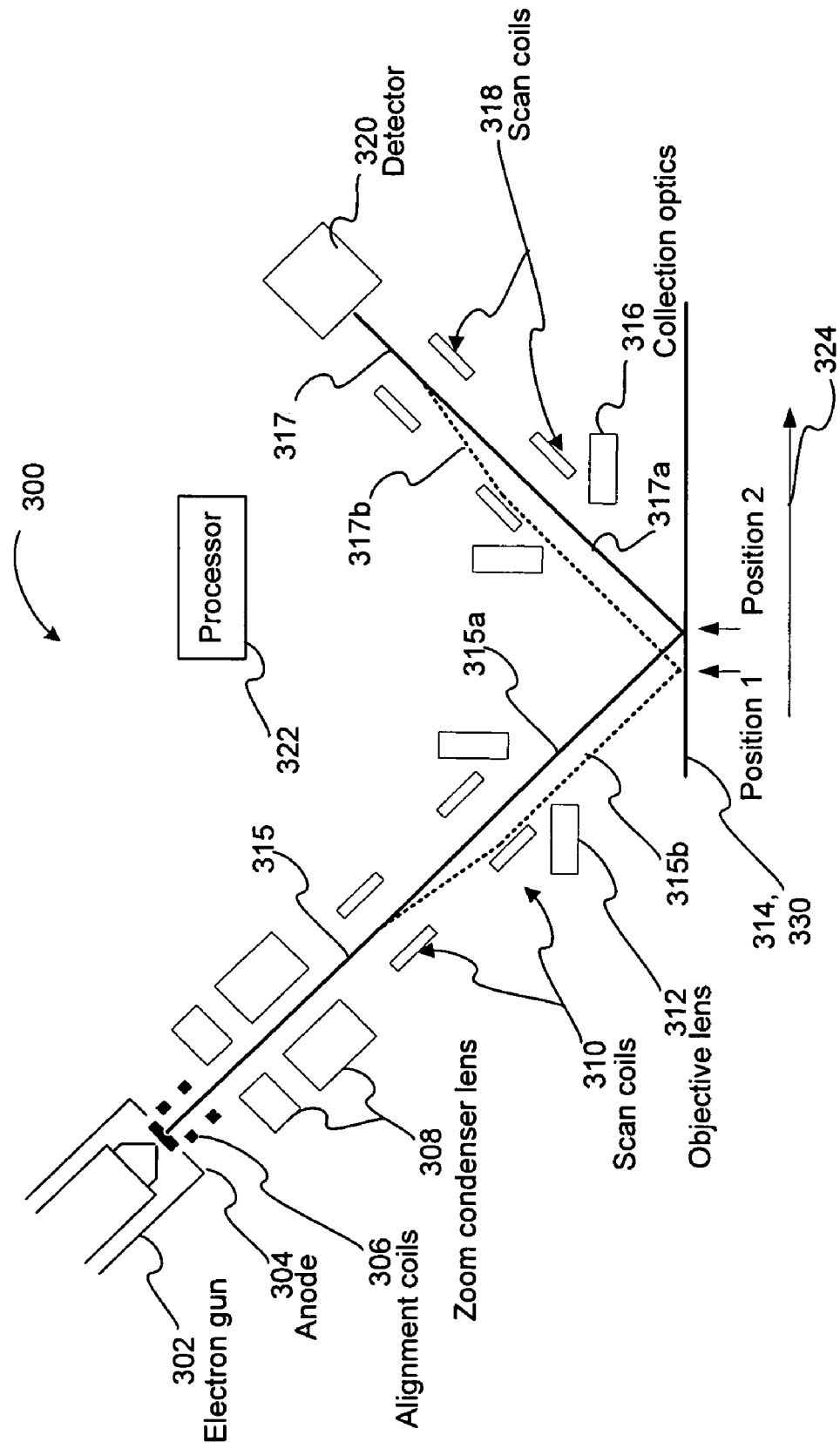
FIG. 3 is a diagrammatic representation of an electron microscopy system in accordance with an alternative implementation of the present invention.

FIG. 3 is a diagrammatic representation of a scanning electron microscopy (SEM) system 300 in accordance with an alternative implementation of the present invention. As shown, the electron microscopy system 300 includes an electron beam source, such as electron gun 302, for generating one or more incident electron beams, e.g., incident beam 315, and an incident scanning system (e.g., alignment coils 306, zoom condenser lens 308, scan coils 310, and objective lens 312) for directing the incident beam towards an area of the sample.

The sample 314 may be positioned on stage 330 that is configured to continuously move along direction 324 while the incident beam 315 impinges on a particular target of the sample 314. The electron microscopy system 300 also includes a detector 320 arranged to detect output beam 317 (secondary electrons and/or backscattered electrons or charged particles) emitted from the sample 314.

In general, the SEM system 300 may include an electron source unit in any suitable form for generating and emitting electrons or charged particles. For example, the source unit may be in the form of an electron gun 302, which includes a filament (or cathode) that is heated such that electrons within the filament are excited and emitted from the filament. The anode 304, e.g., a metal plate with a hole in it, may be maintained or left at ground potential (0 volts) and, accordingly, can have a greatly positive voltage with respect to the cathode. This potential difference can serve to accelerate the electrons toward the anode 304 and out of the electron gun unit 302.

The SEM system 300 may also include one or more alignment coils 306 that can be configured to align the incident electron beam that exits the electron gun with the other components of the SEM system 300 so as to minimize image distortion and loss of resolution. For instance, the alignment coils 306 can be in the form of double-deflection coils (as shown) with a first set of alignment coils that can be configured to introduce a 'tilt' into the incident beam (e.g., changes the angle of incidence) and a second set of alignment coils that can be configured to introduce a second 'tilt' into the incident beam so that the incident beam is adjusted back to its original angle of incidence while being shifted from its original 'axis' of incidence to a new axis. That is, the alignment coils can be configured to shift the incident beam in a plane that is perpendicular to the original axis of incidence. As described further herein, the alignment coils can be utilized (alone or in conjunction with the scanning coils) to escort specific targets on the sample 314 as such specific target continuously moves. Of course, the alignment coils may be configured for only the purpose of alignment adjustment.

The zoom condenser lens 308 and objective lens 312 can be configured to work together so as to focus (and/or magnify or de-magnify) the incident electron beam into a small area or spot on the specimen 314. The size of the spot can be adjusted. In general, since electrons have a charge, their direction of travel can be altered by adjusting the electrostatic and/or magnetic fields with respect to the incident beam. The electromagnetic field intensity of the zoom condenser lens 308 and objective lens 312 are adjusted so as to affect the path of the electrons in the electron beam. The rotational force of the electrons depends on the product of the electron velocity and the density of the magnetic flux. Thus, this vector of the electrons can be adjusted when the strength of the zoom condenser lens 308 and objective lens 312 is changed. The focal length of the various electromagnetic lenses described herein (e.g., condenser lens 308 and objective lens 312) can be controlled by varying the lens current.

The scanning coils 310 can be configured, in principle, in a same manner as described with respect to the alignment coils 306, so as to implement the escorting techniques of the present invention. That is, the scanning coils 310 may be selectively configured so as to escort a particular target specimen as the specimen moves continuously between two positions. As each target is escorted by the incident beam, a same incident angle and beam profile are preferably maintained. In general, the beam deflecting components in a SEM can generally take the form of electromagnets or coils of copper wire that are wrapped around a hollow iron core through which the electrons pass as they are accelerated down a column. By applying a direct current through the copper coil, a magnetic field can be created in the hollow of the core that will slightly change the path of the electron beam, and, thus, the beam path can be controlled by varying the current in the coil, which in turn changes the strength of the electromagnetic field.

The collection optics 316 may generally be configured to direct the output beam towards the detector 320. The collection optics 316 may be configured to focus and accelerate the output beam in a similar manner as outlined above with respect to the condenser and objective lens. The output scan coils 318 can be configurable to deflect the output beam from the escorted target so that the output beam reaches a substantially same area of the detector, regardless of the sample's particular position.

The SEM system 300 may also include an image generator (not shown) arranged to receive the detected signal and generate and/or store an image. The detected signal is then used to generate the image. Thus, the SEM system 300 may also include an analog to digital converter (not shown) for converting the detected signal into a digital signal. The SEM system 300 may also include a processor 322 for processing the image frame data to generate an image of the sample. For example, successive image frame data may be averaged together to create an image that is used to characterize a particular parameter of the escorted target.

The processor 322 may also be operable to control various other aspects of the SEM system 300. In general, the processor 322 may include any suitable hardware, such as one or more computer processing units and/or memory devices, and/or software for controlling various components of the system 300. By way of examples, the processor 322 can be configured to control beam generation, stage movement, incident and output beam movement (e.g., escorting), detector settings, signal processing and analysis, etc.

Although the invention has been described as being implemented on the SEM system 300 of FIG. 3, of course, another SEM system may be implemented. By way of example, the electron source unit may expel electrons at an eV that is substantially equal to the final landing energy value, and the electrons are then accelerated through a series of lens that are set at large positive potentials. As the electrons are expelled from the series of lens, the electrons then slow down and hit the sample at the final landing energy.

Figure 4:
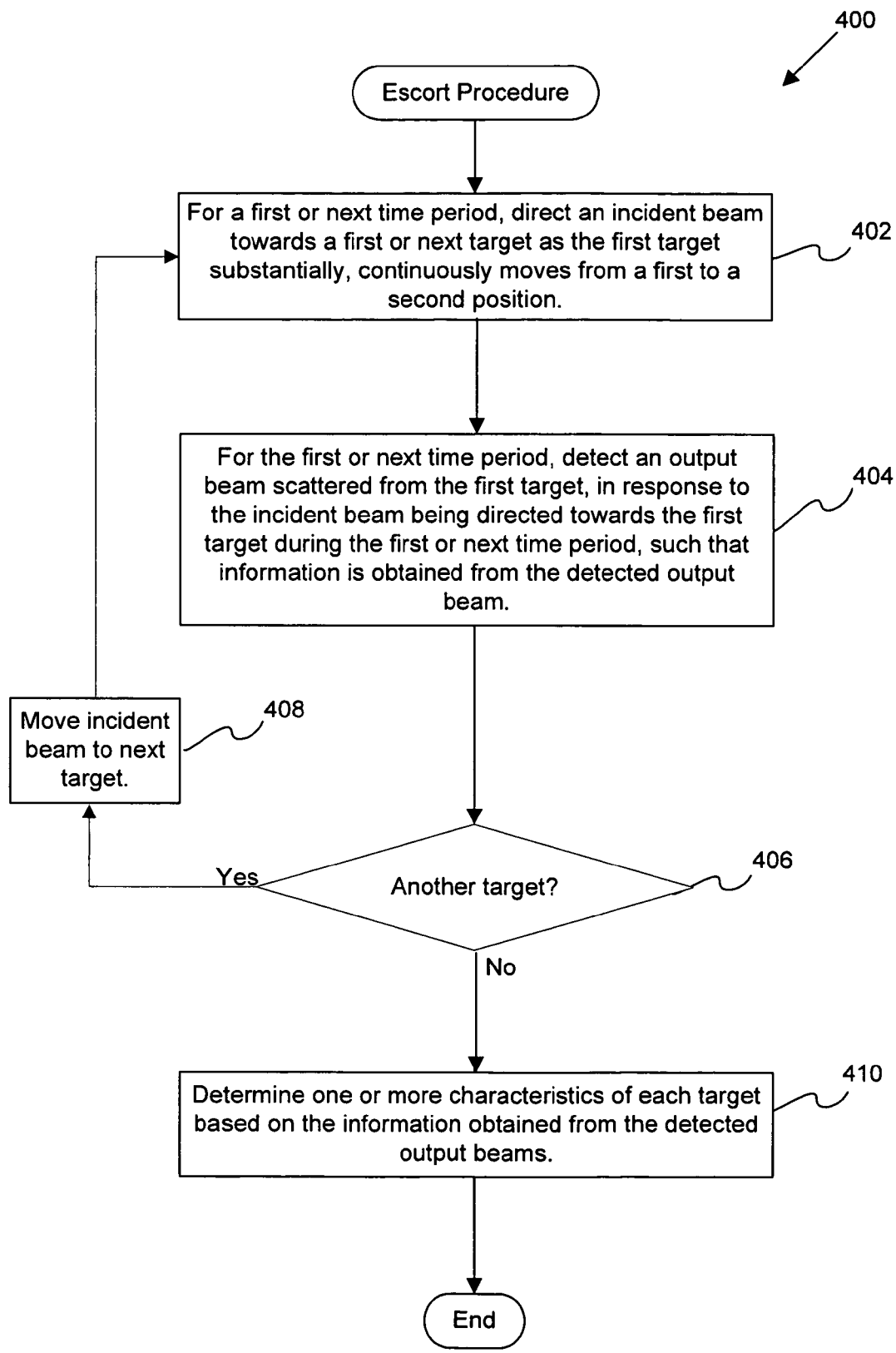
FIG. 4 is a flowchart illustrating a procedure for escorting one or more continuously moving semiconductor targets with an optical or electron beam in accordance with one embodiment of the present invention.

FIG. 4 is a flowchart illustrating a procedure 400 for escorting one or more continuously moving semiconductor targets with an optical or electron beam in accordance with one embodiment of the present invention. For an initial time period, an incident beam is directed towards a first target as the first target substantially, continuously moves from a first position to a second position in operation 402. For this first time period, an output beam that is scattered from the first target, in response to the incident beam being directed towards the first target during the first time period, is detected such that information is obtained from the detected output beam in operation 404.

It is then determined whether there is another target to escort in operation 406. If there is another target, the incident beam is moved to this next target in operations 408. This next target is then escorted in operations 402 and 404. That is, for a next time period, the incident beam is directed towards the next target as the next target substantially, continuously moves from the first position to the second position in operation 402. For this next time period, an output beam that is scattered from the next target, in response to the incident beam being directed towards the next target during the next time period, is detected such that information is obtained from the detected output beam in operation 404.

In one specific implementation, the time periods for different escorted targets are substantially equal. Alternatively, some or all of the escorted targets may have different time periods during which they are escorted. The specific escort duration depends on number factors as outlined herein.

Any number of targets can be escorted using the techniques described herein. After all desired targets are escorted, one or more characteristics of each escorted target may then be determined based on the information, which was obtained from the detected output beams that were detected from the escorted targets, in operations 410. That is, after information is obtained from all of the escorted targets, one or more characteristics may be determined for each of the previously escorted target. Alternatively, one or more characteristics for each target may be determined promptly after each time period in which an individual target is escorted or during such escorting time period.

Any number and type of characteristics, such as an overlay or alignment error, film thickness, critical dimension, etc., may be determined based on one or more output beams that are scattered from a target during a target. In general, one or more properties of an output beam that is detected from a measured target may be analyzed to determine an unknown characteristic's value of such measured target. In one general approach, the values of these one or more detected properties may be compared to a database of property values that have previously been measured from targets having known characteristic values, e.g., from a calibration wafer, or to simulated results. When a substantial match between the currently measured properties and a corresponding set of database properties is found, the measured target is determined to have the characteristic value that is associated with the matching database properties.

In an overlay error example, several approaches to determining overlay from scatterometry measurements concentrate on comparison of the measured spectra to calculated theoretical spectra based on model shape profiles, overlay, and film stack, and material optical properties (n, k dispersion curves), or comparison to a reference signal from a calibration wafer. Alternatively, one or more models that simulate fabrication of targets based on properties that are measured from one or more output beam. Several approaches for determining an overlay error from output beams that are scattered from a set of grating type overlay targets without utilizing a model or a set of calibration data are described in U.S. patent application Ser. No. 10/729,838, filed 5 Dec. 2003 by Walter D. Mieher et al. and U.S. patent application Ser. No. 10/785,396, filed 23 Feb. 2004 by Walter D. Mieher et al., which applications are incorporated herein by reference in their entirety for all purposes.

The escorting techniques and apparatus of the present invention can address the concern that the beam shape may change over large distances, thus, affecting performance (e.g., especially for differential methods). However, if a beam shape change is not a concern, the wafer can remain stationary with the beam spot jumping to each target scan area. The architecture described herein can also enable a scan of angles while leaving the spot position intact. Since the incident and/or output beam angles tend to have an effect on the detected signal, this effect can be used for angle optimization during a training phase to determine an optimum range of angles. A selected angle scan can be implemented over each target to thereby increase the amount of information available for analysis. This increase in information can also entail an increase in accuracy and added applications. Additionally, optimizing the scan angles can be useful in improving tool-to-tool matching.

The techniques of the present invention may be implemented in any suitable combination of software and/or hardware system. Regardless of the system's configuration, it may employ one or more processors for controlling various components of the system and analyzing output images and signals detected with such system. The system also includes one or more memories or memory modules configured to store data, program instructions for the general-purpose inspection operations and/or the inventive techniques described herein. The program instructions may control the operation of an operating system and/or one or more applications, for example. The memory or memories may also be configured to store target images or signals, ROI images or signals, target characteristic values, etc.

Because such information and program instructions may be employed to implement the systems/methods described herein, the present invention relates to machine readable media that include program instructions, state information, etc. for performing various operations described herein. Examples of machine-readable media include, but are not limited to, magnetic media such as hard disks, floppy disks, and magnetic tape; optical media such as CD-ROM disks; magneto-optical media such as floptical disks; and hardware devices that are specially configured to store and perform program instructions, such as read-only memory devices (ROM) and random access memory (RAM). The invention may also be embodied in a carrier wave traveling over an appropriate medium such as air, optical lines, electric lines, etc. Examples of program instructions include both machine code, such as produced by a compiler, and files containing higher level code that may be executed by the computer using an interpreter.

Although the foregoing invention has been described in some detail for purposes of clarity of understanding, it will be apparent that certain changes and modifications may be practiced within the scope of the appended claims. Therefore, the described embodiments should be taken as illustrative and not restrictive, and the invention should not be limited to the details given herein but should be defined by the following claims and their full scope of equivalents.

What is claimed is:

1. A method of inspecting or measuring one or more semiconductor targets, comprising:

directing an incident beam towards a first target as the first target substantially, continuously moves such that the incident beam remains directed at such first target during a first time period in which the first target substantially, continuously moves between a first position and a second position such that a substantially same incident beam angle for the first target is maintained during the first time period;

detecting an output beam scattered from the first target, in response to the incident beam being directed towards the first target during the first time period in which the first target substantially, continuously moves between the first and second positions, such that information is obtained from the detected output beam during the first time period, wherein the first time period is selected so that the information that is collected from the detected output beam during such first time period can be used to determine a characteristic of the first target; and determining the characteristic of the first target based on the detected output beam.

2. A method as recited in claim 1, wherein the incident beam is an optical beam.

3. A method as recited in claim 2, wherein directing the incident beam at the first target during the first time period is accomplished by titling one or more illumination mirrors in a path of the incident beam so that the incident beam's movement is synchronized with the first target's continuous movement between the first and second positions so that the information, that can be used to determine a characterization of the first target, is obtained from the detected output beam during the first time period.

4. A method as recited in claim 3, wherein detecting the output beam from the first target during the first time period is accomplished by titling one or more output mirrors in a path of the output beam so that the output beam is detected by a same area of detector during the first time period.

5. A method as recited in claim 1, wherein the incident beam is an electron beam.

6. A method as recited in claim 5, wherein directing the incident beam at the first target during the first time period is accomplished by configuring an incident scanning system in a path of the incident beam so that the incident beam's movement is synchronized with the first target's substantially, continuous movement between the first and second positions so that the information, that can be used to determine a characterization of the first target, is obtained from the detected output beam during the first time period.

7. A method as recited in claim 6, wherein detecting the output beam from the first target during the time period is accomplished by configuring an output scanning system in a path of the output beam so that the output beam is detected by a same area of detector during the first time period.

8. A method as recited in claim 1, wherein the characteristic is an overlay error.

9. A method as recited in claim 1, wherein the characteristic of the first target includes one or more of the following: an overlay error, a film thickness, or a critical dimension measurement.

10. A method as recited in claim 1, further comprising:

after the first time period, directing the incident beam towards a second target as the second target substantially, continuously moves such that the incident beam remains directed at such second target during a second time period in which the second target moves between the first position and the second position;

detecting an output beam scattered from the second target, in response to the incident beam being directed towards the second target during the second time period in which the second target moves between the first and second positions, such that information is obtained from the detected output beam during the second time period, wherein the second time period has a substantially equal duration as the first time period and is selected so that the information that is obtained from the detected output beam during such second time period can be used to determine a characteristic of the second target; and determining the characteristic of the second target based on the detected output beam from the second target.

11. A method as recited in claim 10, wherein the incident beam is initially directed at the second target when the second target is at a substantially same position as the first target's position at which the incident beam was initially directed towards the first target.

12. An apparatus for inspecting or measuring one or more semiconductor targets, comprising:

one or more processors;

one or more memory, wherein at least one of the processors and memory are configured for causing the apparatus to:

direct an incident beam towards a first target as the first target substantially, continuously moves such that the incident beam remains directed at such first target during a first time period in which the first target substantially, continuously moves between a first position and a second position such that a substantially same incident beam angle for the first target is maintained during the first time period;

detect an output beam scattered from the first target, in response to the incident beam being directed towards the first target during the first time period in which the first target substantially, continuously moves between the first and second positions, such that information is obtained from the detected output beam during the first time period, wherein the first time period is selected so that the information that is collected from the detected output beam during such first time period can be used to determine a characteristic of the first target; and determine the characteristic of the first target based on the detected output beam.

13. An apparatus as recited in claim 12, wherein the incident beam is an optical beam.

14. An apparatus as recited in claim 13, further comprising one or more illumination mirrors positioned in a path of the incident beam, wherein directing the incident beam at the first target during the first time period is accomplished by configuring the one or more illumination mirrors so that the incident beam's movement is synchronized with the first target's continuous movement between the first and second positions so that the information, that can be used to determine a characterization of the first target, is obtained from the detected output beam during the first time period.

15. An apparatus as recited in claim 14, further comprising one or more output mirrors positioned in a path of the output beam, wherein detecting the output beam from the first target during the first time period is accomplished by configuring the one or more output mirrors so that the output beam is detected by a same area of detector during the first time period.

16. An apparatus as recited in claim 12, wherein the incident beam is an electron beam.

17. An apparatus as recited in claim 16, further comprising an incident scanning system, wherein directing the incident beam at the first target during the time period is accomplished by configuring the incident scanning system so that the incident beam's movement is synchronized with the first target's substantially, continuous movement between the first and second positions so that the information, that can be used to determine a characterization of the first target, is obtained from the detected output beam during the first time period.

18. An apparatus as recited in claim 17, further comprising an output scanning system, wherein detecting the output beam from the first target during the time period is accomplished by configuring the output scanning system so that the output beam is detected by a same area of detector during the first time period.

19. An apparatus as recited in claim 12, wherein the characteristic is an overlay error.

20. An apparatus as recited in claim 12, wherein the characterization includes one or more of the following: an overlay error, a film thickness, or a critical dimension measurement.

21. An apparatus as recited in claim 12, wherein at least one of the processors and memory are further configured for causing the apparatus to:

after the first time period, direct the incident beam towards a second target as the second target substantially, continuously moves such that the incident beam remains directed at such second target during a second time period in which the second target moves between the first position and the second position;

detect an output beam scattered from the second target, in response to the incident beam being directed towards the second target during the second time period in which the second target moves between the first and second positions such that information is obtained from the detected output beam during the second time period, wherein the second time period has a substantially equal duration as the first time period and is selected so that the information that is obtained from the detected output beam during such second time period can be used to determine a characteristic of the second target; and determine the characteristic of the second target based on the detected output beam from the second target.

22. An apparatus as recited in claim 21, wherein the incident beam is initially directed at the second target when the second target is at a substantially same position as the first target's position at which the incident beam was initially directed towards the first target.

* * * * *